US007706852B2

(12) United States Patent
Baker, Jr.

(10) Patent No.: US 7,706,852 B2
(45) Date of Patent: Apr. 27, 2010

(54) SYSTEM AND METHOD FOR DETECTION OF UNSTABLE OXYGEN SATURATION

(75) Inventor: Clark R. Baker, Jr., Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1093 days.

(21) Appl. No.: 11/343,147

(22) Filed: Jan. 30, 2006

(65) Prior Publication Data

US 2007/0179369 A1 Aug. 2, 2007

(51) Int. Cl.
*A61B 5/1455* (2006.01)

(52) U.S. Cl. ...................................... 600/323
(58) Field of Classification Search .......... 600/309–344
See application file for complete search history.

(56) References Cited

U.S. PATENT DOCUMENTS

| | | | |
|---|---|---|---|
| 4,106,503 A | 8/1978 | Rosenthal et al. |
| 4,365,636 A | 12/1982 | Barker |
| 4,523,279 A | 6/1985 | Sperinde |
| 4,630,614 A | 12/1986 | Atlas |
| 4,651,746 A | 3/1987 | Wall |
| 4,738,266 A | 4/1988 | Thatcher |
| 4,757,824 A | 7/1988 | Chaumet |
| 4,765,340 A | 8/1988 | Sakai et al. |
| 4,802,485 A | 2/1989 | Bowers et al. |
| 4,869,253 A | 9/1989 | Craig |
| 5,134,995 A | 8/1992 | Gruenke et al. |
| 5,199,424 A | 4/1993 | Sullivan |
| 5,206,807 A | 4/1993 | Hatke |
| 5,233,983 A | 8/1993 | Markowitz |
| 5,275,159 A | 1/1994 | Griebel |
| 5,303,699 A | 4/1994 | Bonassa et al. |
| 5,318,597 A | 6/1994 | Hauck et al. |
| 5,335,654 A | 8/1994 | Rapoport |
| 5,353,788 A | 10/1994 | Miles |
| 5,368,026 A | 11/1994 | Swedlow et al. |
| 5,385,144 A | 1/1995 | Yamanishi et al. |
| 5,398,682 A | 3/1995 | Lynn |
| 5,483,969 A | 1/1996 | Testerman |
| 5,485,847 A | 1/1996 | Baker, Jr. |

(Continued)

FOREIGN PATENT DOCUMENTS

DE 9 200 422.9 7/1992

(Continued)

OTHER PUBLICATIONS

Hornero et al. Approximate Entropy from Overnight Pulse Oximetry for the Obstructive Sleep Apea Syndrome, Sep. 2005, IEEE, Proceeding of 2005 IEEE Engineering of Medicine and Biology 27th Anual Conference.*

(Continued)

*Primary Examiner*—Eric F Winakur

(57) ABSTRACT

Methods and systems are described for simplified detection of unstable oxygen saturation of a patient by analysis of statistical variations in blood oxygen. One method for automatic detection of unstable oxygen saturation of a patient using a pulse oximeter comprises receiving at least a single time series input of oxygen saturation values and computing at least two metrics based on statistical properties of the single time series input of the oxygen saturation values.

29 Claims, 10 Drawing Sheets

U.S. PATENT DOCUMENTS

| | | |
|---|---|---|
| 5,485,851 A | 1/1996 | Erickson |
| 5,490,502 A | 2/1996 | Rapoport et al. |
| 5,535,739 A | 7/1996 | Rapoport et al. |
| 5,540,733 A | 7/1996 | Testerman et al. |
| 5,549,106 A | 8/1996 | Gruenke et al. |
| 5,551,419 A | 9/1996 | Froehlich et al. |
| 5,605,151 A | 2/1997 | Lynn |
| 5,632,270 A | 5/1997 | O'Mahony et al. |
| 5,645,053 A | 7/1997 | Remmers et al. |
| 5,645,054 A | 7/1997 | Cotner et al. |
| 5,682,878 A | 11/1997 | Ogden |
| 5,704,345 A | 1/1998 | Berthon-Jones |
| 5,730,144 A | 3/1998 | Katz et al. |
| 5,740,795 A | 4/1998 | Brydon |
| 5,743,250 A | 4/1998 | Gonda et al. |
| 5,743,263 A | 4/1998 | Baker, Jr. |
| 5,751,911 A | 5/1998 | Goldman |
| 5,765,563 A | 6/1998 | Vander Schaaf |
| 5,769,084 A | 6/1998 | Katz et al. |
| 5,782,240 A | 7/1998 | Raviv et al. |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport et al. |
| 5,823,187 A | 10/1998 | Estes et al. |
| 5,827,179 A | 10/1998 | Lichter et al. |
| 5,830,135 A | 11/1998 | Bosque et al. |
| 5,845,636 A | 12/1998 | Gruenke et al. |
| 5,853,364 A | 12/1998 | Baker, Jr. et al. |
| 5,865,173 A | 2/1999 | Froehlich |
| 5,865,736 A | 2/1999 | Baker, Jr. et al. |
| 5,891,023 A | 4/1999 | Lynn |
| 5,902,250 A | 5/1999 | Verrier et al. |
| 5,957,885 A | 9/1999 | Bollish |
| 6,006,379 A | 12/1999 | Hensley |
| 6,015,388 A | 1/2000 | Sackner et al. |
| 6,035,223 A | 3/2000 | Baker, Jr. |
| 6,083,156 A | 7/2000 | Lisiecki |
| 6,083,172 A | 7/2000 | Baker, Jr. et al. |
| 6,105,575 A | 8/2000 | Estes et al. |
| 6,120,441 A | 9/2000 | Griebel |
| 6,138,675 A | 10/2000 | Berthon-Jones |
| 6,144,877 A | 11/2000 | DePetrillo |
| 6,148,814 A | 11/2000 | Clemmer et al. |
| 6,216,032 B1 | 4/2001 | Griffin et al. |
| 6,223,064 B1 | 4/2001 | Lynn et al. |
| 6,286,508 B1 | 9/2001 | Remmers et al. |
| 6,299,581 B1 | 10/2001 | Rapoport et al. |
| 6,305,374 B1 | 10/2001 | Zdrojkowski et al. |
| 6,342,039 B1 | 1/2002 | Lynn et al. |
| 6,345,619 B1 | 2/2002 | Finn |
| 6,367,474 B1 | 4/2002 | Berthon-Jones et al. |
| 6,371,113 B1 | 4/2002 | Tobia et al. |
| 6,401,713 B1 | 6/2002 | Hill et al. |
| 6,411,833 B1 | 6/2002 | Baker, Jr. et al. |
| 6,425,861 B1 | 7/2002 | Haberland et al. |
| 6,463,326 B1 | 10/2002 | Hartley et al. |
| 6,488,634 B1 | 12/2002 | Rapoport et al. |
| 6,502,572 B1 | 1/2003 | Berthon-Jones et al. |
| 6,519,486 B1 | 2/2003 | Edgar, Jr. et al. |
| 6,529,752 B2 | 3/2003 | Krausman et al. |
| 6,532,960 B1 | 3/2003 | Yurko |
| 6,539,940 B2 | 4/2003 | Zdrojkowski et al. |
| 6,609,016 B1 | 8/2003 | Lynn |
| 6,609,517 B1 | 8/2003 | Estes et al. |
| 6,622,726 B1 | 9/2003 | Du |
| 6,637,434 B2 | 10/2003 | Noble |
| 6,640,806 B2 | 11/2003 | Yurko |
| 6,675,797 B1 | 1/2004 | Berthon-Jones |
| 6,691,705 B2 | 2/2004 | Dittmann et al. |
| 6,721,584 B2 | 4/2004 | Baker, Jr. et al. |
| 6,745,764 B2 | 6/2004 | Hickle |
| 6,748,252 B2 | 6/2004 | Lynn |
| 6,760,608 B2 | 7/2004 | Lynn |
| 6,761,167 B1 | 7/2004 | Nadjafizadeh et al. |
| 6,780,427 B2 | 8/2004 | Baker, Jr. et al. |
| 6,804,656 B1 | 10/2004 | Rosenfeld et al. |
| 6,807,965 B1 | 10/2004 | Hickle |
| 6,814,074 B1 | 11/2004 | Nadjafizadeh et al. |
| 6,817,361 B2 | 11/2004 | Berthon-Jones et al. |
| 6,832,200 B2 | 12/2004 | Greevan et al. |
| 6,836,679 B2 | 12/2004 | Baker, Jr. et al. |
| 6,896,660 B2 | 5/2005 | Jelliffe et al. |
| 6,932,084 B2 | 8/2005 | Estes et al. |
| 6,948,497 B2 | 9/2005 | Zdrojkowski et al. |
| 6,988,498 B2 | 1/2006 | Berthon-Jones |
| 7,398,115 B2 * | 7/2008 | Lynn .......................... 600/324 |
| 2002/0117173 A1 | 8/2002 | Lynn et al. |
| 2002/0190863 A1 | 12/2002 | Lynn |
| 2003/0000522 A1 | 1/2003 | Lynn et al. |
| 2003/0127097 A1 | 7/2003 | Yurko |
| 2003/0158466 A1 | 8/2003 | Lynn |
| 2004/0073098 A1 | 4/2004 | Geva et al. |
| 2004/0138540 A1 | 7/2004 | Baker, Jr. et al. |
| 2004/0158135 A1 | 8/2004 | Baker, Jr. et al. |
| 2004/0170154 A1 | 9/2004 | Carter et al. |
| 2004/0181134 A1 | 9/2004 | Baker, Jr. et al. |
| 2004/0230105 A1 | 11/2004 | Geva et al. |
| 2005/0016536 A1 | 1/2005 | Rapoport et al. |
| 2005/0027207 A1 | 2/2005 | Westbrook et al. |
| 2005/0081854 A1 | 4/2005 | Nadjafizadeh et al. |
| 2005/0085735 A1 | 4/2005 | Baker, Jr. et al. |
| 2005/0124871 A1 | 6/2005 | Baker, Jr. et al. |
| 2005/0143634 A1 | 6/2005 | Baker, Jr. et al. |
| 2005/0197549 A1 | 9/2005 | Baker, Jr. |
| 2005/0197552 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0240091 A1 | 10/2005 | Lynn |
| 2006/0025931 A1 | 2/2006 | Rosen et al. |
| 2006/0189880 A1 | 8/2006 | Lynn |

FOREIGN PATENT DOCUMENTS

| | | | |
|---|---|---|---|
| EP | | 0459284 B1 | 1/1995 |
| EP | | 0651971 A1 | 10/1995 |
| EP | | 0709107 A1 | 5/1996 |
| EP | | 0714670 A2 | 6/1996 |
| EP | | 0722747 A2 | 7/1996 |
| EP | | 0788805 A3 | 5/1998 |
| EP | | 0968734 A3 | 1/2000 |
| EP | | 1004325 A3 | 6/2000 |
| EP | | 0700690 B1 | 2/2002 |
| EP | | 0759791 B1 | 8/2002 |
| EP | | 0934723 B1 | 9/2004 |
| EP | | 1172123 B1 | 10/2004 |
| EP | | 0875258 B1 | 11/2004 |
| EP | | 1488743 A2 | 12/2004 |
| EP | | 1491135 | 12/2004 |
| JP | | 3170866 | 7/1991 |
| JP | | 3238813 | 10/1991 |
| JP | | 4332536 | 11/1992 |
| JP | | 7124138 | 5/1995 |
| JP | | 7136150 | 5/1995 |
| JP | | 2003194714 | 7/2003 |
| JP | | 2003210438 | 7/2003 |
| JP | | 2004008572 | 1/2004 |
| JP | | 2004113353 | 4/2004 |
| JP | | 2004194908 | 7/2004 |
| JP | | 2004248819 | 9/2004 |
| JP | | 2004290545 | 10/2004 |
| JP | | 27319247 A2 | 12/2007 |
| JP | | 28161657 A2 | 7/2008 |

| | | |
|---|---|---|
| WO | WO 88/01149 | 2/1988 |
| WO | WO 90/09146 | 8/1990 |
| WO | WO 90/14121 | 11/1990 |
| WO | WO9101678 | 2/1991 |
| WO | WO 92/11054 | 7/1992 |
| WO | WO 92/22244 | 12/1992 |
| WO | WO9309711 | 5/1993 |
| WO | WO 94/06499 | 3/1994 |
| WO | WO 94/23780 | 10/1994 |
| WO | WO 95/32016 | 11/1995 |
| WO | WO 97/14462 | 4/1997 |
| WO | WO 97/28838 | 8/1997 |
| WO | WO9843071 | 10/1998 |
| WO | WO 99/24099 | 5/1999 |
| WO | WO9932030 | 7/1999 |
| WO | WO 99/45989 | 9/1999 |
| WO | WO0021438 | 4/2000 |
| WO | WO 00/67827 | 11/2000 |
| WO | WO 2004/047621 A2 | 6/2004 |
| WO | WO 2005/065757 A1 | 7/2005 |

OTHER PUBLICATIONS

Abraham, Howard et al., Sequential Cardiorespiratory Patterns in Septic Shock, Critical Care Medicine, vol. 11, No. 10, Oct. 1983, pp. 799-803.
Agilent Technologies, Agilent M1165/66/67/75/76/77A Component Monitoring System and Agilent M1205A V24 & V26, User's Reference Manual, vol. 1, System Information, Part No. M1046-9101L, First Ed., Printed Nov. 2000.
Agilent Technologies, Agilent M1165/66/67/75/76/77A Component Monitoring System and Agilent M1205A V24 & V26, User's Reference Manual, vol. 2, Parameter Information, Part No. M1046-9101L, First Ed., Printed Nov. 2000.
Alaris System, Brochure, Medication Safety System Focused at the Point of Care, Cardinal Health, Alaris Products, pp. 8.
Aubry, et al., The $SaO_2$/t Diagram as A Useful Means To Express Nocturnal Hypoxemia, Chest, 1989; 96: 1341-45.
Bartolo, Anton, et al., An Arrhythmia Detector and Heart Rate Estimator For Overnight Polysomnography Studies, conditionally accepted for IEEE Transactions, 19 pages.
Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.
Blackshear et al., Nocturnal Dyspnea And Atrial Fibrillation Preset Cheyne—Stokes Respirations In Patients With Congestive Heart Failure, Jun. 26, 1995, Arch Intern Med. vol. 155, p. 1296-1302.
Buckle, Patricia, et al., Polysomnography in Acutely Ill Intensive Care Unit Patients, Chest, v. 102 n.1, p. 288 (4), American College of Chest Physicians.
Daley, Denise M., MD, Beware of All Sedatives in Patients With Sleep Apnea, Anesthesia Patient Safety Foundation Newsletter and posted on the Malpractice company's web site. The Doctors Company | Sleep Apnea and Narcotic Postoperative Pain . . . http://www.thedoctors.com/risk/bulletines/sleepapnea.asp.
Dowdell, WT; Javaheri, S; McGinnis, W, Cheyne-Stokes Respiration Presenting as Sleep Apnea Syndrome. Clinical and Polysomnographic Features, Am Rev Respir Dis, Apr. 1990, pp. 871-879.
Dyken, Mark Eric et al., Obstructive Sleep Apnea Associated with Cerebral Hypoxemia and Death, Neurology 2004; 62, pp. 491-493.
Epstein et al., "Cost-Effectivess Analysis Of Nocturnal Oximetry As A Method Of Screening For Sleep Apnea-Hypopnea Syndrome," Jan. 1, 1998, Chest, vol. 113, pp. 97-103*.
Evans, et al., A Microcomputer System for Monitoring and Analysing Oxyhemolobin Saturation During Sleep. Computer Programs in Biomedicine, 1984; 18: 227-234.
Fisher, Kyle S., MD, Value of Pulse Oximetry Monitoring On the Ward is Questioned, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.
Fletcher et al., Effect of Cardiac Output Reduction on Rate of Desaturation in Obstructive Apnea; Chest, 99:452-456, 1991.
Fletcher et al., Rate of Oxyhemoglobin Desaturation in Obstructive versus Nonobstructive Apnea; Am Rev Respi Dis. 143:657-660; 1990.
Fletcher et al., The Rate of Fall of Arterial Oxyhemoglobin Saturation in Obstructive Sleep Apnea, Chest, 1989; 96: 717-722.
Forster, Robert E., The Lung, Physiologic basis of Pulmonary Function Tests (Book), 1986 Year Book medical Publishers, Inc., Chapter 3, I. Volume of Pulmonary Ventilation, pp. 32-64.
Gagnadoux, Fredrick et al., Home Unattended vs Hospital Telemonitored Polysomnography in Suspected Obstructive Sleep Apnea Syndrome: A Randomized Crossover Trial, Chest 2002; 121; 753-758.
Gami, Apoor S. et al., Day-Night Pattern of Sudden Death in Obstructive Sleep Apnea, The New England Journal of Medicine, 2005; 352, pp. 1206-1214.
George et al., Identification on Qualification of Apneas by Computer-based Analysis of Oxygen Saturation, American Review of Respiratory Disease, 1988; 137; 1238-1240.
Griffiths, et al., A Video System for Investigating Breathing Disorders During Sleep, Thorad, 1991; 46: 136-140.
Guilleminault et al., Sleep Apnea Syndrome: Can It Induce Hemodynamic Changes?, Western Journal of Medicine, vol. 123, Jul. 1975, pp. 7-16.
Guilleminault, C. et al., Unattended CPAP Titration: Toward A Smart Medicine, May 20, Stanford University Sleep Research Center, 1 page.
Gyulay et al., A Comparison of Clinical Assessment and Home Oximetry in the Diagnosis of Obstructive Sleep Apnea, American Review of Respiratory Disease, 1993; 147: 50-53.
Hoch, et al., Uberprufung der Fruherkennungsmethode MESAM und Biox 3700 zur Erfassung Schlafbezogener Atmmgmsergulationsstorungen bei jungen Mannern, Pneumologie, 1991; 45: 217-222 (and translation).
Hoffarth, et al., Beuteilung Pulsoximetrisch Erfasster zklisheer . . . and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: 229-232.
Jain, Sanjay S., et al., Perioperative Treatment of Patients with Obstructive Sleep Apnea, Current Opinion Pulmonary Medicine 10, pp. 482-488.
Keyl, C., et al., Spektralanalyse von Arterieller Sauerstoff-sättigung und RR-Intervallen bei Patienten mit obstrukitver Schlafapnoe, Wein Med Wschr 1995, pp. 515-516 (vol. 145).
Kirby et al., Computer Quantitation of Saturation Impairment Time As An Index of Oxygenation During Sleep, Com Meth, 1992: 107-115.
Koehler, U., et al., Nocturnal Myocardial Ischemia and Cardiac Arrhythmia in Patients with Sleep Apnea with and Without Coronary Heart Disease (1991) 69; 474-482.
Longobardo et al., Sleep Apnea Considered As A Control System Instability, Sep. 1982, Respiratory Physiology 50: 311-333.
Lynn, Lawrence A., Cluster Analysis: A New Technology for the Evaluation of Oximetry and Airflow Waveforms in Obstructive Sleep Apnea, Accepted after revision on Dec. 20, 1997, 17 total pages.
Pae, Eung-Kwon, et al., Neuroscience Letters 375, 2005, pp. 123-128.
Patil, Ramesh S. et al., Application of An Artificial Intelligence Program to Therapy of High-Risk Surgical Patients, New Horizons, vol. 4, No. 4, pp. 541-550.
Pepin et al., Does Oximetry contribute to the Detection of Apneic Events? Mathematical. Processing of the $SaO_2$ Signal, Chest, May 1991; 99: 1151-1157.
Rapoport, et al., CO2 Homeostasis During Periodic Breathing: Predictions From A Computer Model, The American Journal of Applied Physiological, 1993, vol. 75, Issue 5, pp. 2302-2309.
Rauscher et al., Computerized Detection of Respiratory Events During Sleep from Rapid Increases in Oxyhemoglobin Saturation, Lung, 1991; 169: 355-42.

Rauscher et al., Quantification of sleep-disordered breathing by computerized analysis of oximetry, heart rate, and snoring, Eur Respir J. Jun. 1991; 4: 655-659.

Ryan, Clodagh M., et al., Periodicity of Obstructive Sleep Apnea in Patients With and Without Heart Failure, Chest 2005; 127, pp. 536-542.

Salmi, et al., Evaluation of Automatic Analysis of SCSB, Airflow and Oxygen Saturation Signals in Patients with Sleep Related Apneas, Chest, 1989; 96: 255-61.

Sanders et al., Obstructive Sleep Apnea Teated by Independently Adjusted Inspiratory and Expiratory Positive Airway Pressures via Nasal Mask, Chest, 1990: 98: 317-24.

Scharf, Steven M., et al., Cardiovascular Effects of Periodic Occlusions of the Upper Airways in Dogs, American Review of Respiratory Disease, pp. 321-329.

Series, et al., Influence of Continuous Positive Airways Pressure on Sleep Apnea-Related Desaturation in Sleep Apnea Patients, Lung, 1992; 170: 281-290.

Series et al., Utility of Nocturnal Home Oximetry for Case Finding in Patients with Suspected Sleep apnea Hypopnea Syndrome, Sep. 15, 1993, Annals of Internal Medicine, col. 119, p. 449-453.*

Shepard, J., Gas Exchange and Hemodynamics During Sleep, Medical Clinicals of North America, vol. 69, No. 6, Nov. 1985, pp. 1243-1265.

Shoemaker, W. C. et al., Incidence, Physiologic Description, Compensatory Mechanisms, and Therapeutic Implications of Monitored Events, Critical Care Medicine, Dec. 1989, vol. 17, No. 12, pp. 1277-1285.

Shoemaker, W. C. et al., Multicenter study of noninvasive monitoring systems as alternatives to invasive monitoring of acutely ill emergency patients, Chest, 1998; vol. 114; pp. 1643-1652.

Shoemaker, W. C. et al., Noninvasive Physiologic Monitoring of High-Risk Surgical Patients, Archives of Surgery, vol. 131, No. 7, Jul. 1996, pp. 732-737.

Shoemaker, W. C. et al., Prediction of Outcome and Severity of Illness by Analysis of the Frequency Distributions of Cardiorespiratory Variables, Critical Care Medicine, vol. 5, No. 2, Mar.-Apr. 1977, pp. 82-88.

Shoemaker, W. C. et al., Sequence of Physiologic Patterns in Surgical Septic Shock, Critical Care Medicine, Dec. 21, 1993 (12): pp. 1821.

Shoemaker, W. C., Cardiorespiratory Patterns in Complicated and Uncomplicated Septic Shock: Physiologic Alterations and Their Therapeutic Implications, Ann. Surg., Jul. 1971, vol. 174, No. 1, pp. 119-125.

Shoemaker, W. C., Early Physiologic Patterns in Acurate Illness and Accidents: Toward A Concept of Circulatory Dysfunction and Shock Based on Invasive and Noninvasive Hemodynamic Monitoring, New Horizons, Nov. 1996, vol. 4, No. 4, pp. 395-412.

Shoemaker, W.C., Oxygen Transport and Oxygen Metabolism in Shock and Critical Illness, Invasive and Noninvasive Monitoring of Circulatory Dysfunction and Shock, Critical Care Clinics, vol. 12, No. 4, Oct. 1996, pp. 939-969.

Shoemaker, W. C., Temporal Physiologic Patterns of Shock and Circulatory Dysfunction Based on Early Descriptions by Invasive and Noninvasive Monitoring, New Horizons, vol. 4, No. 2, May 1996, pp. 300-318.

Slutsky et al., Quantification of Oxygen Saturation During Episodic Hypoxemia, American Review of Respiratory Disease, 1980; 121:893-895.

Staniforth, AD; Kinnear, WJ; Starling, R; Cowley AJ, Nocturnal desaturation in Patients with Stable Heart Failure, Heart, Apr. 1998; pp. 394-399.

Strohl et al., Oxygen Saturation During Breath Holding and During Apneas in Sleep, Chest, Feb. 1984: 85, No. 1; 181-186.

Svanborg, et al., A Limited diagnostic Investigation for Obstructive Sleep Apnea Syndrome: Oximetry and Static Charge Sensitive Bed, Chest, 1990; 98: 1341-45.

Tan and T. H. Koh, Evaluation of Obstructive Sleep Apnea in Singapore Using Computerized Polygraphic Monitoring, Annals Academy of Medicine, Mar. 1991, vol. 20 No. 2, pp. 196-200.

Tatevossian, Raymond G., et al., Noninvasive Hemodynamic Monitoring for Early Warning of Adult Respiratory Distress Syndrome in Trauma Patients, Journal of Critical Care, vol. 15, No. 4 (Dec. 2000), pp. 151-159.

Tatevossian, Raymond G., et al., Transcutaneous oxygen and C02 as early warning of tissue hypoxia and hemodynamic shock in critically ill emergency patients.

Timms et al., Oxygen Saturation by Oximetry: analysis By Microcomputer, Journal of Polysomographic Technology, Spring 1988: 13-21.

Timms, et al., and Profox Associates, Inc., Profox for the Bedside, Version 8SP Nov. 1992, Programs for Oximetry [IBM], User's Manual, Nov. 1992, 20 total pages.

White, D. P., et al., Assessment of Accuracy and Analysis Time of a Novel Device to Monitor Sleep and Breathing in the Home, Sleep, vol. 18, No. 2, Feb. 1995, pp. 115-126.

Wilkins, Robert L., et al., EGAN's Fundamentals of Respiratory Care, Analysis and Monitoring of Gas Exchange, Book, Eighth Edition, Chapter 16, Section III, Capnography/Capnometry During Mechanical Ventilation, pp. 383-389.

Wilkinson, M. H., et al., Effect of Venous Oxygenation on Arterial Desaturation Rate During Repetitive Apneas in Lambs, Respiration Physiology 101 (19950 321-331).

Williams, et al., Screening for Sleep Apnea Using Pulse Oximetry and A Clinical Score, Chest, 100/3, Sep. pp. 631-635.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20$^{th}$ Annual International conference of the IEEE Engie in Medicine and Biology Society*, vol. 20, No. 6, p. 3072-3075, 1998.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

J. Huang, et al.; "Low Power Motion Tolerant Pulse Oximetry," *Abstracts*, A7, p. S103. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

R. Neumann, et al.; "Fourier Artifact suppression Technology Provides Reliable $SpO_2$," *Abstracts*, A11, p. S105. (undated).

* cited by examiner

SYSTEM AND METHOD FOR DETECTION OF UNSTABLE OXYGEN SATURATION

BACKGROUND OF THE INVENTION

The present invention generally relates to medical methods and systems, particularly for the detection of unstable oxygen saturation of a patient.

Obstructive sleep apnea is recognized as one of the most common disorders in the United States. The lower oxygen levels associated with obstructive sleep apnea play a major role in cardiovascular morbidity including cardiac arrest and stroke. Obstructive sleep apnea causes characteristic patterns of gradual oxygen de-saturation, followed by rapid re-saturation when a sleeping patient's body manages to briefly increase muscle tone in the upper airway to sufficiently resume respiration. This pattern tends to repeat cyclically at roughly similar periods and saturation amplitudes. Millions of patients experience such characteristics of sleep apnea for years at a time without being diagnosed or treated as acute health consequences do not readily arise. Despite the fact that obstructive sleep apnea is easily treated, both the patient and the family are often completely unaware of the presence of this dangerous condition as anything more than heavy snoring.

Obstructive sleep apnea often develops as patients enter middle age and begin to snore. The major cause is an increase in fat deposition in the neck which results in narrowing of the airway. When the muscle tone of the upper airway diminishes during sleep, negative pressure associated with inspiration through this narrow airway results in collapse of the upper airway which effectively chokes off all air movement and a fall in oxygen. The fall in oxygen produces central nervous system stimulation contributing to hypertension, potential heart and blood vessel injury, and finally results in arousal of the patient. Upon arousal, increase in airway muscle tone opens the upper airway and the patient rapidly inhales and ventilates quickly to correct the low oxygen levels. Generally, the arousal is brief and the patient is not aware of the arousal.

Undiagnosed obstructive sleep apnea can lead to serious consequences, including progressive decline in heart muscle function, blood vessel damage, and even death by stroke or cardiac arrest.

Detection of such profound physiologic instability may be accomplished by conventional polysomnography. However, this approach is expensive and difficult to implement on a sufficient scale. Further diagnosis approaches for detecting obstructive sleep apnea with the use of oximetry systems are described by the following U.S. Pat. Nos. 5,398,682; 5,605,151; 5,891,023; 6,223,064; 6,342,039; 6,609,016; 6,748,252; 6,760,608 and U.S. Patent Publication Nos. 2002/0190863; 2003/0000522; 2003/0158466, the full disclosures of which are incorporated herein by reference. A number of these references are directed to analyzing waveshapes of various signals.

Alternative diagnostic methods and systems for identifying sleep apnea that do not require evaluation of a patient by polysomnography or the analysis of a succession of specific events could be advantageous.

BRIEF SUMMARY OF THE INVENTION

A method for automatic detection of unstable saturation of a patient using a pulse oximeter is provided. At least a single time series input of oxygen saturation values (e.g., $SpO_2$) is received and at least two metrics are computed based on statistical properties of the single time series input of oxygen saturation values. In one embodiment, the statistical metrics are then averaged and a relationship determined between the statistical metrics. An output is provided if the relationship exceeds a threshold value, wherein the threshold value is indicative of cyclic saturation variations. In one embodiment, the ratio of the average saturation changes over fifteen second intervals to the average saturation changes over one second intervals is calculated. Small changes are disregarded, and remaining ones with a ratio above a threshold slope indicate possible sleep apnea or hypopnea. Generally, cyclic saturation variations may be detected with a period in the range from one minute to five minutes. Some cyclic saturation variations may be detected in periods as short as 35 to 50 seconds.

Methods and systems of the present invention provide for simplified detection of unstable oxygen saturation of a patient by analysis of statistical variations in blood oxygen. In particular, the present invention provides physiologic signal processing systems and oximetry software algorithms that allow for the detection of obstructive sleep apnea, ventilation instability, airway instability, breathing arrhythmia, hypopnea, and like conditions.

The output from the methods and systems of the present invention may comprise a report, record data, or alarm generation. Alarm management may also comprise various outputs, including an audio alarm, a visual alert, or a print-out so as to inform the patient, nurse, physician, etc. of the detected unstable saturation variations and this potentially risky physiologic condition. It will further be appreciated that the metrics of the statistical properties of the single $SpO_2$ time series may additionally be modified based on one or more signal quality metrics internal to a oximetry algorithm so that the simplified detection methods of the present invention are not easily fooled by non-physiologic artifacts. For example, challenging conditions such as patient motion, low perfusion, or interference from other electronic devices may be screened out so as not to trigger a false alarm.

The statistical metrics may comprise a magnitude of oxygen saturation changes over half second to thirty second intervals. A first metric comprises a magnitude of saturation changes over one second intervals or five second intervals. A second metric comprises a magnitude of saturation changes over ten second intervals or fifteen second intervals. Still further the statistical metrics may comprise a skewness of the single time series input of oxygen saturation values and a kurtosis of the single time series input of oxygen saturation values. The skewness of a distribution is a measure of its asymmetry in relation to a normal distribution. The kurtosis of a distribution is a measure of the shape of the distribution around the mean. The statistical metrics may be associated with ventilation or airway instability, particularly obstructive sleep apnea. It will be appreciated that the receiving, computing, modifying, averaging, determining, and providing steps of the oximetry software algorithm are carried out by a processor.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE

Exemplary embodiments of the present invention may provide patient monitoring systems and methods for automatic detection of unstable oxygen saturation of a patient using a pulse oximeter so as to diagnose obstructive sleep apnea. Exemplary embodiments of the present invention may be adapted to use single time series inputs of oxygen saturation values from non-invasive pulse oximeters (e.g., $SpO_2$) or data taken from invasive measurements such as measurements of arterial oxygenation saturation values (e.g., $SaO_2$). Moreover, data obtained by either technique allows analysis of statistical variations in blood oxygenation so as to detect unstable oxygen saturation. Pulse oximeters that may be used with exemplary systems and methods of the present invention include pulse oximeters commercially available from Nellcor Puritan Bennett Incorporated of Pleasanton, Calif., the assignee of the present application.

Figure 1A:
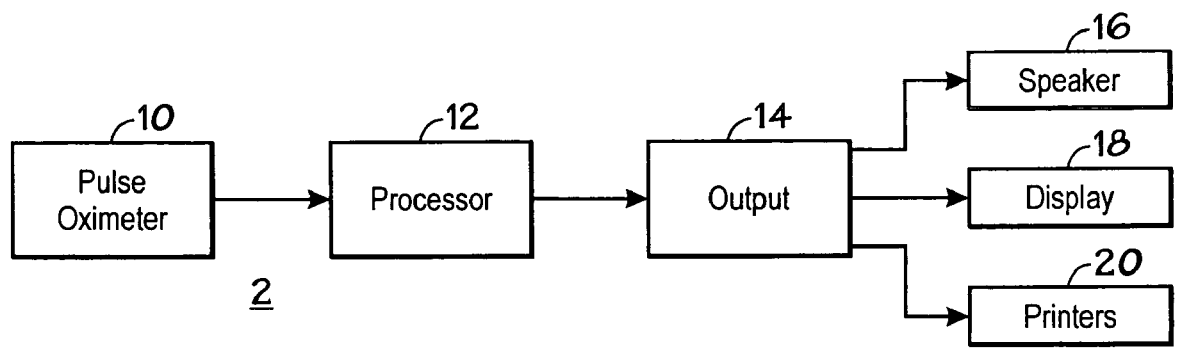
FIG. 1A is a simplified block diagram illustrating a patient monitoring apparatus in accordance with the principles of the present invention.
Figure 1B:
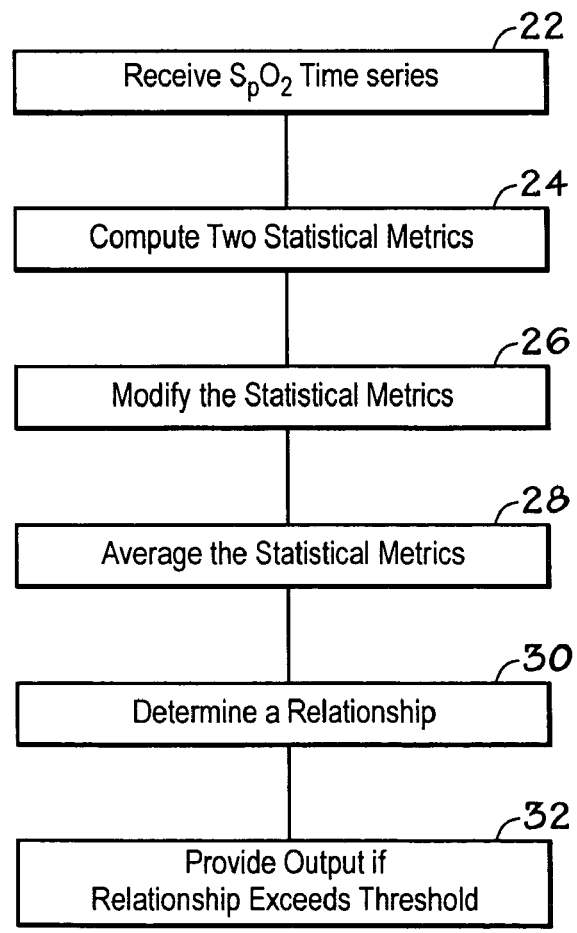
FIG. 1B is a simplified flow chart illustrating a method for automatically detecting unstable oxygen saturation of a patient in accordance with the principles of the present invention.

Referring now to FIG. 1A, a simplified block diagram illustrates a patient monitoring system 2. FIG. 1B illustrates a method for automatically detecting unstable oxygen saturation of a patient in accordance with the principles of the present invention. The system 2 includes an input device, namely a pulse oximeter 10, a processor 12 electronically coupled to the pulse oximeter 10, and output buffer 14 electronically coupled to the processor 12. The output buffer 14 is adapted to deliver data to at least one of a plurality of output devices, such as a speaker 16, a display screen 18, or a printer 20.

The oximetry software algorithm for automatic detection of unstable saturation of a patient using a pulse oximeter is carried out by the processor 12. As shown at block 22 (FIG. 1B), at least a single time series input of oxygen saturation values is received. Examples of sources of the oxygen saturation values include the pulse oximeter 10 (FIG. 1A), as during a real-time monitoring of a patient, or from a data file created at an earlier time. As shown by block 24 (FIG. 1B), at least two metrics are computed based on statistical properties of the single time series input of oxygen saturation values. The statistical metrics are modified based on one or more signal quality metrics as indicated by block 26, averaged as indicated by block 28, and a relationship determined between the statistical metrics as indicated by block 30. For example, the relationship may be the ratio of one of the statistical metrics to another of the statistical metrics. The relationship may be defined to correspond to a known condition, such as a disordered breathing condition like obstructive sleep apnea. An output is provided if a numerical representation of the relationship exceeds a threshold value as indicated by block 32. The threshold value may be an arbitrarily chosen value indicative of a predetermined level of cyclic saturation variations. Exemplary embodiments of the present invention do not require detection of one or more specific $SpO_2$ events, measurement of the amplitude or period of such events, or the use of any additional physiologic monitors or parameters.

Generally, cyclic saturation variations may be detected with a period in the range from one minute to five minutes. Some cyclic saturation variations may be detected in periods as short as 35 to 50 seconds or even shorter, depending on lung capacity of the patient, for example, or other factors. Alarm management may comprise various outputs, including sounding an audio alarm through the speaker 16, displaying a visual alert on the display screen 18, or providing a print-out from the printer 20 so as to inform the patient, nurse, physician or the like of the detected unstable saturation variations.

Examples of statistical metrics that may be employed in conjunction with exemplary embodiments of the present invention include a magnitude of saturation changes over one second intervals, a magnitude of saturation changes over five second intervals, a magnitude of saturation changes over ten second intervals, or a magnitude of saturation changes over fifteen second intervals. Generally, combinations of the statistical metrics may be chosen to take into account both magnitude and frequency range of variations in a physiologic parameter of interest (i.e., oxygen saturation) to evaluate the overall repetitiveness of changes. For example, the obstructive sleep apnea may be effectively identified by taking into account the combination of a relatively short change (e.g., one second) and a relatively longer change (e.g., five, ten, or fifteen seconds). It will be appreciated however that several other statistical metrics may also be used with the to identify cyclic saturation variations characteristic of airway instability, particularly obstructive sleep apnea. Examples of other statistical metrics include processing the frequency content of the single time series input of oxygen saturation values using a Fast Fourier Transform, autocorrelation of the saturation values, or derivatives. Because re-saturation is characteristically much faster than de-saturation, the derivative of the reported saturation should have a positive skewness when measured over a period of several minutes. To the extent that these cyclic saturation variations exhibit a relatively repetitive magnitude, both the saturations and their derivatives should have a more negative kurtosis than for non-cyclic saturation variations.

The processor 12 (FIG. 1A) may include or be coupled to a memory device that contains exemplary code for an oximetry software algorithm, exemplary code for audio alarms, exemplary code for visual alerts, or the like. The processor 12 and output devices (e.g., speaker 16, display 18, printer 20) may be disposed in a common housing with the pulse oximeter 10 to form a single integrated system. Alternatively, pulse oximeter 10, the processor 12, the output buffer 14 and various output devices 16, 18, 20 may all comprise separate independent components operatively coupled to one another. An alternative embodiment may include a subset of the pulse oximeter 10, the processor 12, the output buffer 14 and one or more of the output devices 16, 18, 20 disposed in a single housing with one or more of the remaining devices disposed externally thereto.

Figure 2:
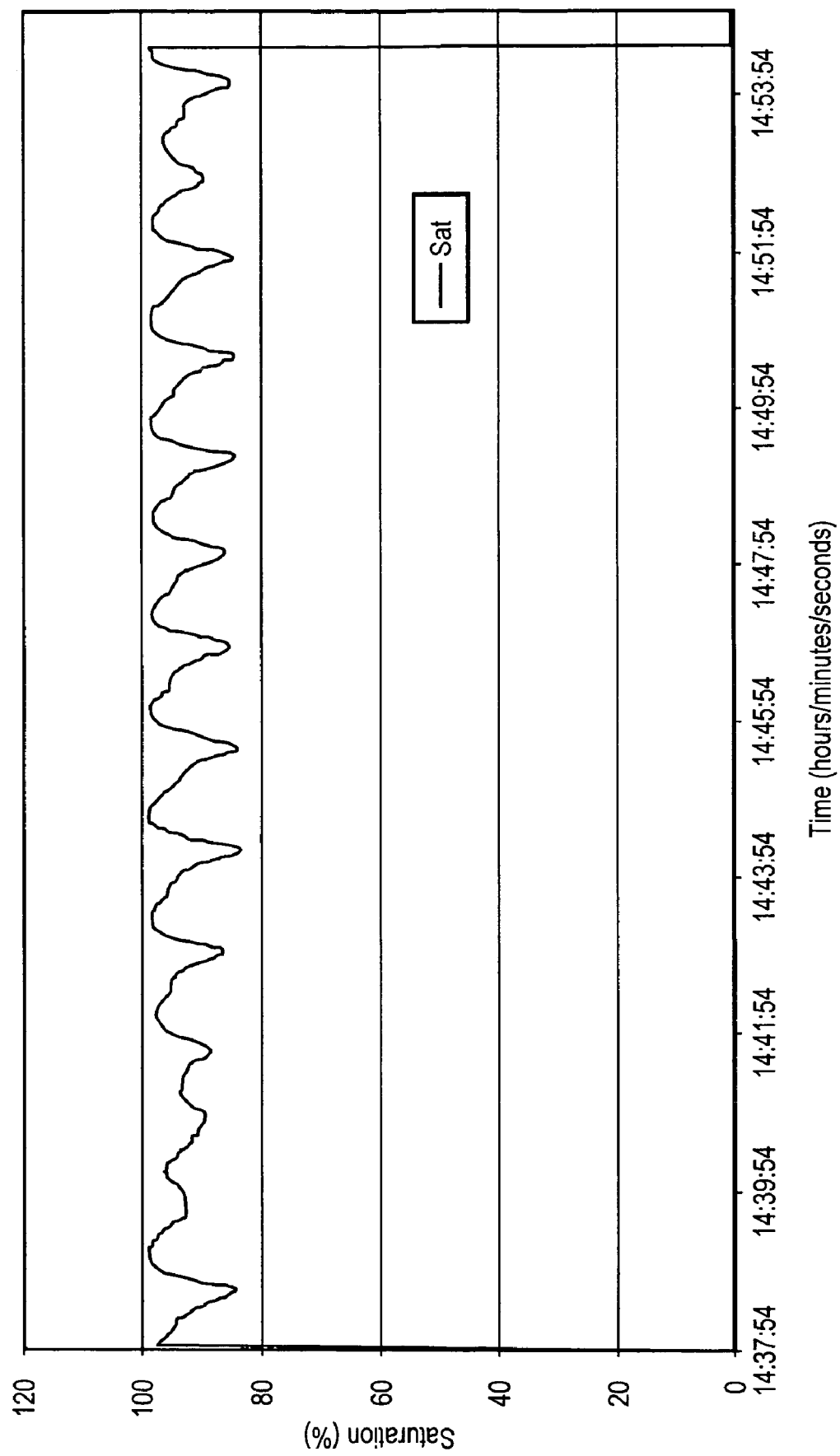
FIG. 2 graphically illustrates cyclic saturation variations characteristic of obstructive sleep apnea.
Figure 3:
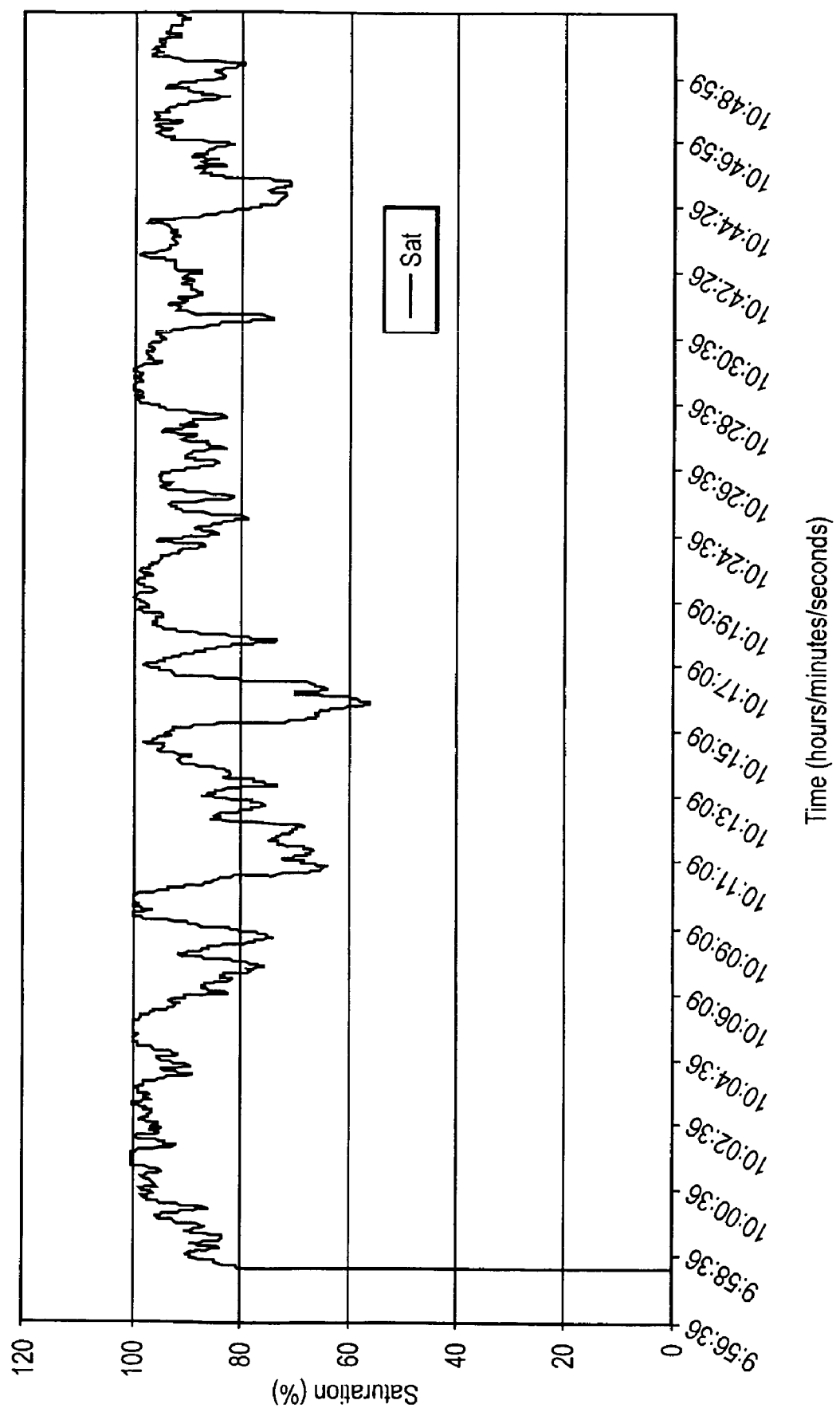
FIG. 3 graphically illustrates saturation variations due to artificial artifacts such as motion, low perfusion, or other interference.

FIG. 2 is representative of unstable oxygen saturation behavior where the saturation changes smoothly within a period of approximately more than a minute. It will be appreciated that challenging oximetry conditions were also identified in all age groups from newborn infants to adults. Examples of such artificial artifacts include motion, low perfusion, arrhythmia, dicrotic notches, interference from other electronic devices and the like. FIG. 3 is representative of saturation variations that are primarily due to motion artifacts where the SpO$_2$ variations are quite irregular and often shorter in duration.

Figure 4:
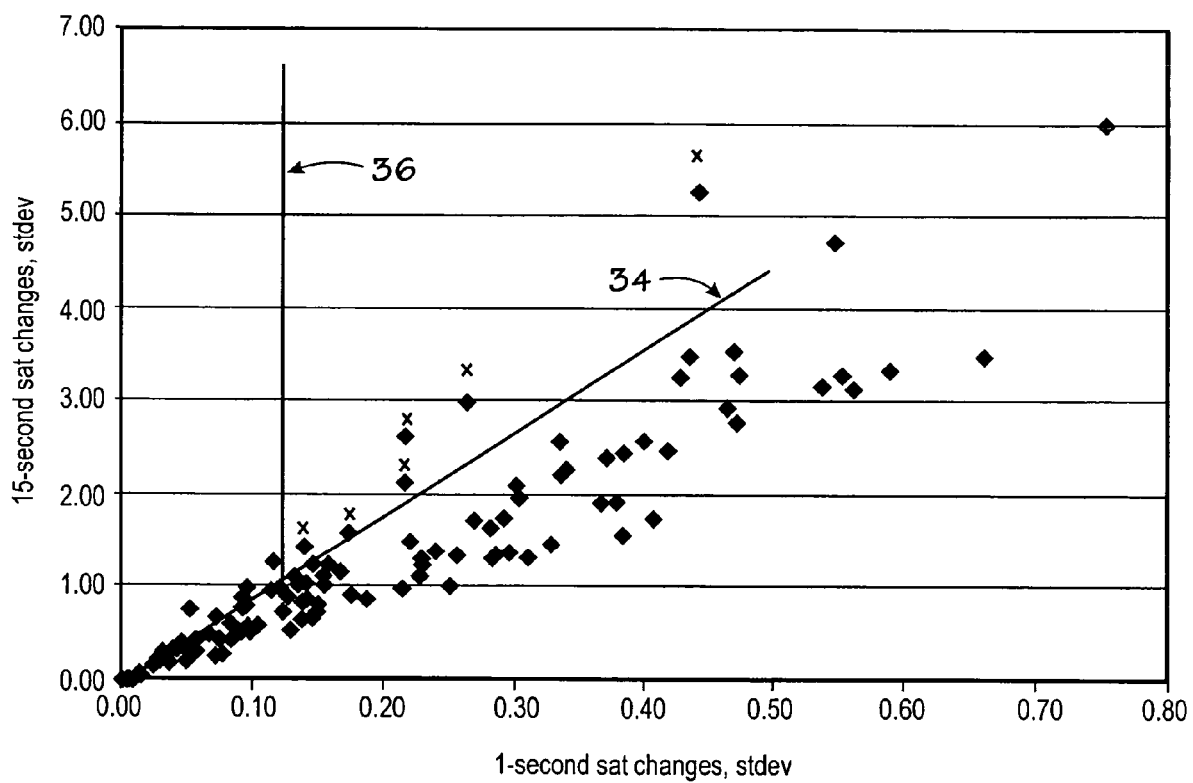
FIG. 4 is a graph showing a relationship between two metrics computed from statistical properties of $SpO_2$ time series in accordance with an exemplary embodiment of the present invention.

FIG. 4 is a graph that shows a plot of a plurality of datasets that have been analyzed in accordance with an exemplary embodiment of the present invention. To create the plot shown in FIG. 4, an empirical analysis was performed by post-processing a set of sample oximetry data. The sample data, which comprised empirically obtained oximetry data obtained from 113 patients over a wide range of conditions, was post-processed using an oximetry algorithm known as 05CI, which was implemented in a model N595 pulse oximeter. Each post-processed saturation output was manually examined by a skilled individual to identify datasets of patients whose oxygen saturation data exhibited cyclic de-saturations. In particular, six patients whose datasets were included in the sample database were identified as indicative of cyclic de-saturations characteristic of obstructive sleep apnea.

Referring now to FIG. 4, a relationship between two metrics computed from statistical properties of time series input of oxygenation saturation values for all 113 patients represented in the sample database is plotted. In particular, statistical metrics of saturation variations that relate both to overall magnitude and frequency were utilized. On the x-axis, the magnitude of saturation changes over one second intervals is plotted. On the y-axis, the magnitude of saturation changes over fifteen second intervals is plotted. For these metrics, magnitude may be represented by a number of methods, including either the absolute difference between two saturation values (e.g., $|S_1-S_2|$) or the by the square root of the square of the differences (e.g., $\sqrt{(S_1-S_2)^2}$). These two metrics and a standard deviation (i.e., the root mean square of the differences) were calculated, averaged, and plotted for each of the separate one hundred thirteen cases, as illustrated in FIG. 4.

Significantly, as shown in FIG. 4, the results of this investigation indicate that the six datasets that were determined by empirical manual analysis to represent a cyclic pattern of unstable oxygen saturation are clearly identifiable in FIG. 4. Each of these six datasets is identified by an 'x' in FIG. 4. Moreover, all six 'x' datasets are above a diagonal threshold line 34 in FIG. 4. The diagonal threshold 34 is an arbitrary line that is intended to correspond to a predetermined level of cyclic physiologic activity represented by a dataset under consideration. As steeper slopes are chosen for the diagonal threshold 34, fewer datasets are identified as exceeding the threshold (i.e. being above the threshold). As shallower slopes are chosen for the diagonal threshold, more datasets are identified as exceeding the threshold. For the selected set of time intervals illustrated in FIG. 4, the slope of the diagonal threshold line 34 was empirically determined to be about 9. As seen in FIG. 4, this choice of threshold values results in identification of the datasets empirically determined to represent cyclically unstable oxygen saturation. This threshold could be employed with new databases of datasets that have not been empirically evaluated, with the result that datasets having the same level of cyclic physiologic activity would be identified without the need of empirical analysis of the new data.

If the y-axis plotted magnitude of saturation changes over five or ten second intervals, the slope of the diagonal threshold line 34 will be about 4.5 to 9. Hence, a slope of the diagonal threshold line 34 will be in a range from about 60% (e.g., 9/15) to about 90% (e.g., 4.5/5) of the ratio of time intervals used for quantifying saturation changes. The diagonal threshold line indicates a preponderance of longer-term saturation variation indicative of physiologic instability.

An arbitrary vertical threshold 36 may also be employed to avoid identifying datasets that exceed the threshold line 34, but that nonetheless comprise statistical variations that are sufficiently small as to be categorized as minimal and not of interest. In FIG. 4, the vertical threshold 36 was selected so that the six datasets empirically determined to correspond to cyclic unstable variations in oxygen saturation are to the right of the vertical threshold 36 and above the threshold line 34. Thus, the results illustrated in FIG. 4 indicate a clear metric separation of the six cases empirically determined to correspond to cyclic variations indicative of obstructive sleep apnea from the other 107 datasets. This illustrates the effectiveness of the statistical metric analysis of FIG. 1B to adequately detect unstable oxygen saturation. FIG. 4 thus represents the construction of a framework of threshold values that may be employed to evaluate other datasets to identify datasets indicative of a cyclic pattern of unstable oxygen saturation. Such cyclic patterns of unstable oxygen saturation may correspond to sleep disordered breathing such as obstructive sleep apnea.

FIGS. 5-10 are graphical representations of exemplary patient data indicative of cyclically unstable oxygen saturation. One hundred thirteen sets of patient data were manually evaluated for the presence of an indication of a cyclic desaturation pattern. Of those 113 datasets, six were determined to comprise cyclic variations. Each of the graphs shown in FIGS. 5-10 each correspond to one of those six datasets. The same six datasets were subsequently identified by a computer program comprising an exemplary embodiment of the present invention. Hence, these results show the effectiveness of the statistical metric analysis set forth in FIG. 1B to effectively predict unstable oxygen saturation.

In an exemplary embodiment of the present invention, the data is identified as indicative of an instability during all periods in which a predetermined threshold value is exceeded. This indication may comprise setting a variable to a value indicative of instability when data exceeding the threshold value is being evaluated. The variable may be set to a value indicative of no instability at other times.

Figure 5:
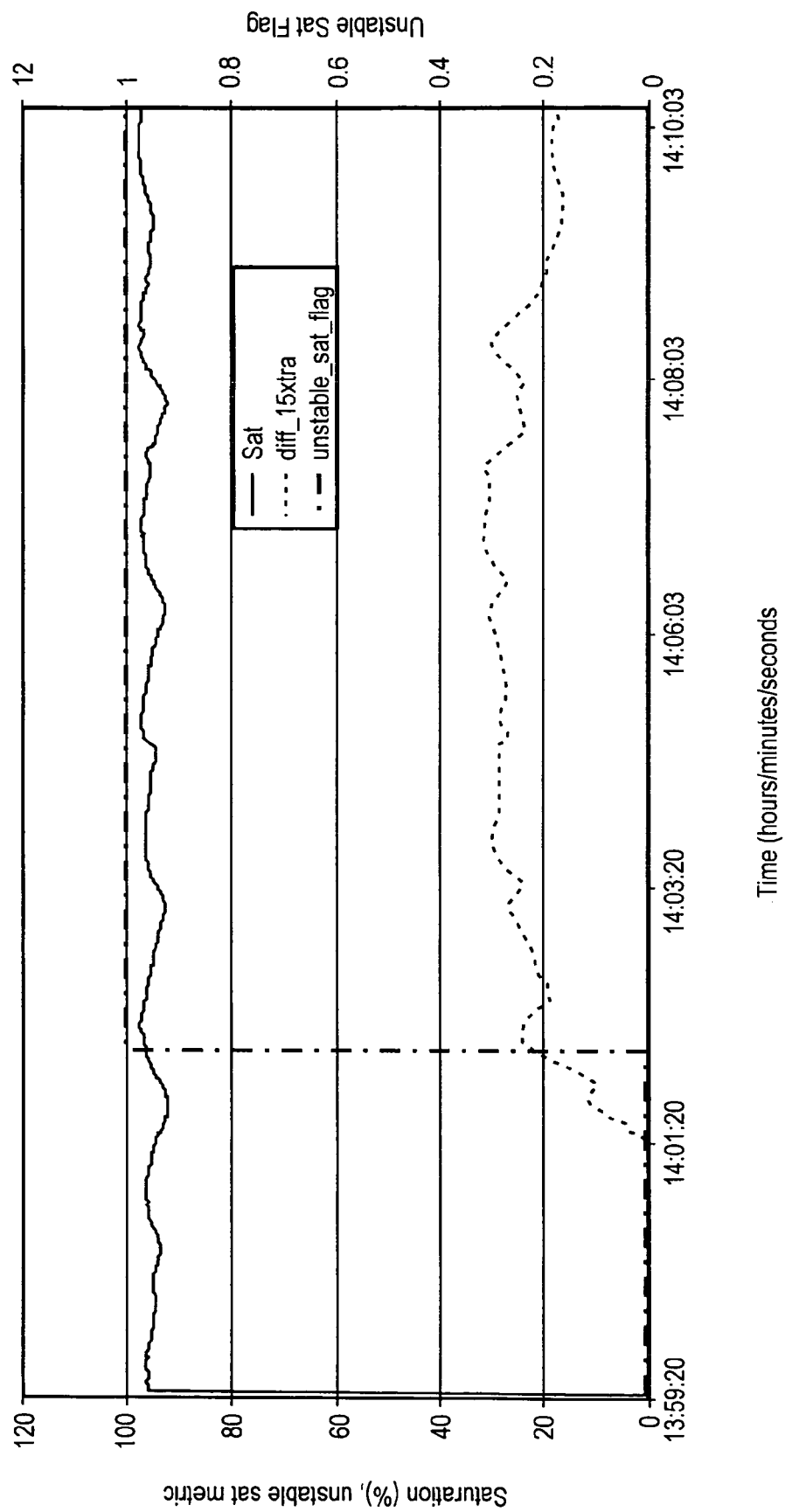
FIGS. 5 through 10 are graphical representations showing exemplary data output in accordance with an embodiment of the present invention.
Figure 6:
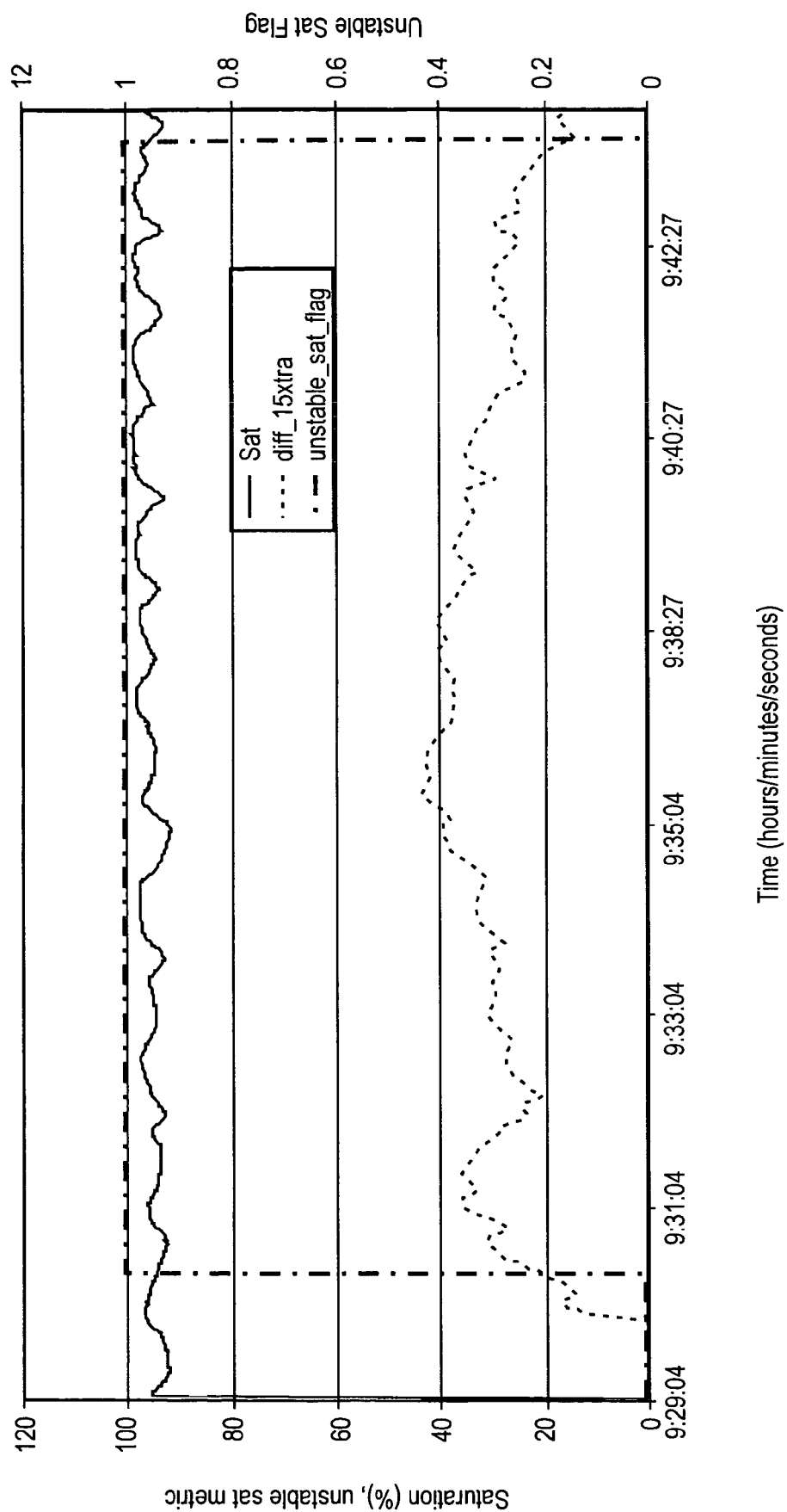
Figure 7:
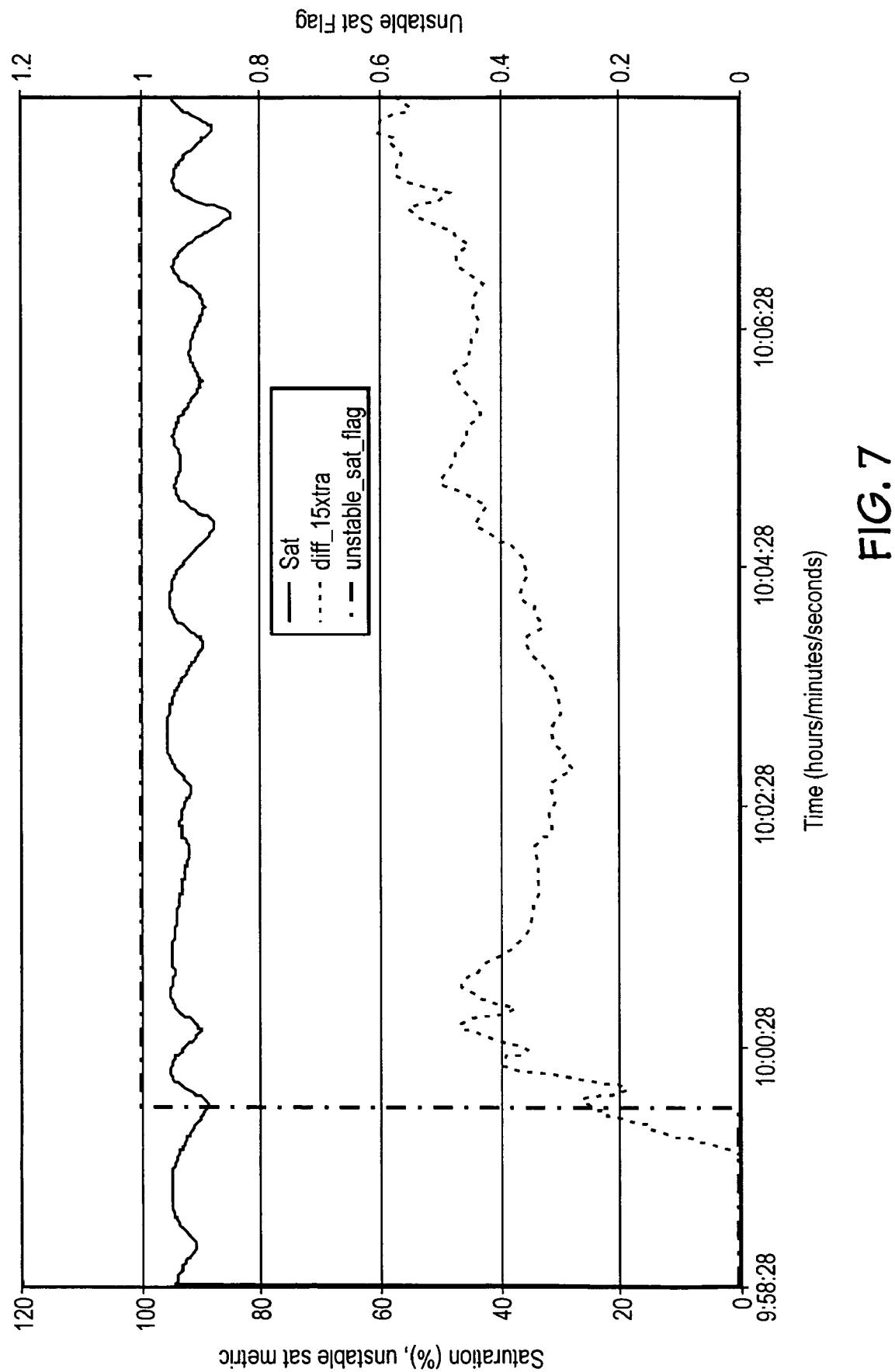
Figure 8:
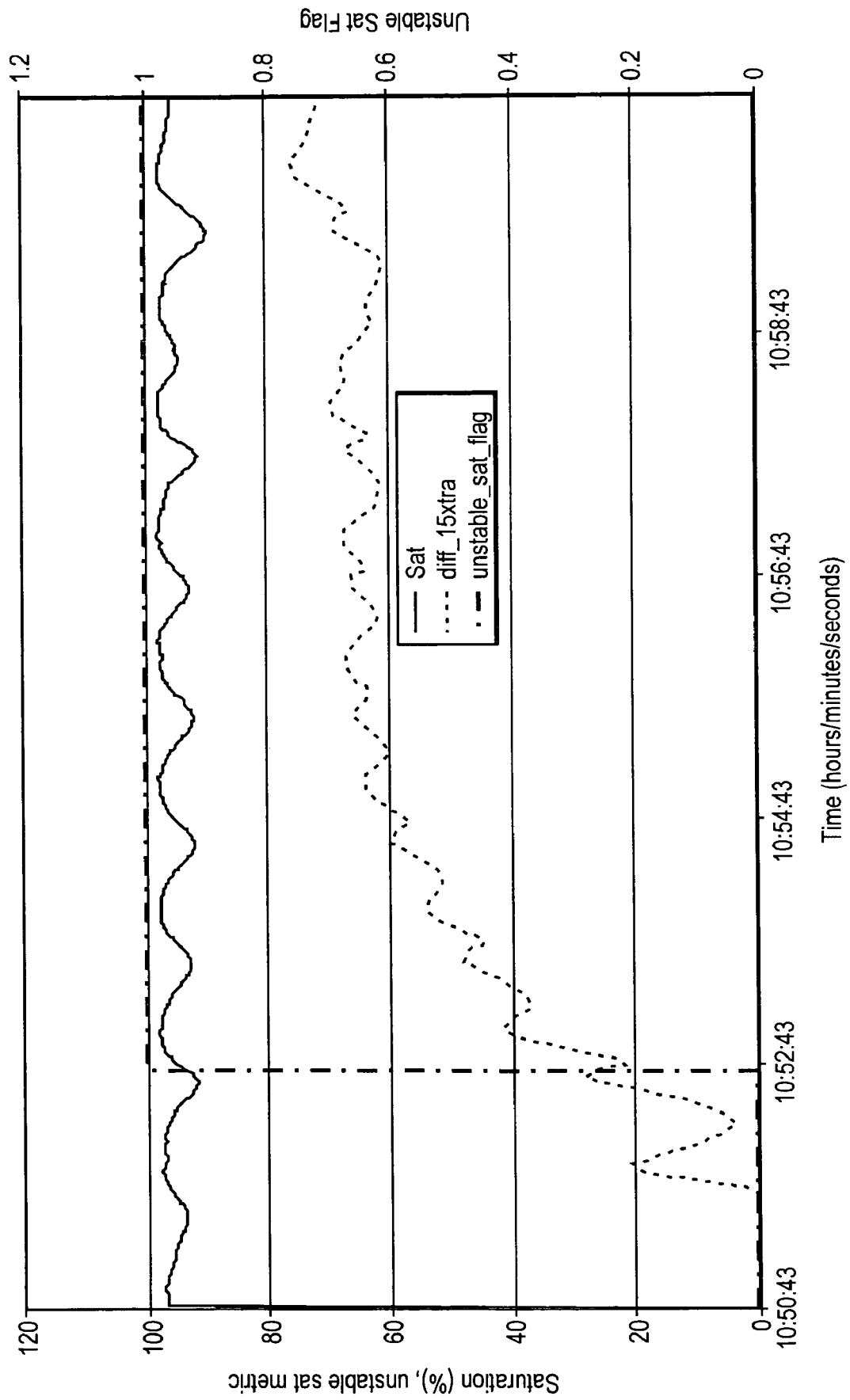
Figure 9:
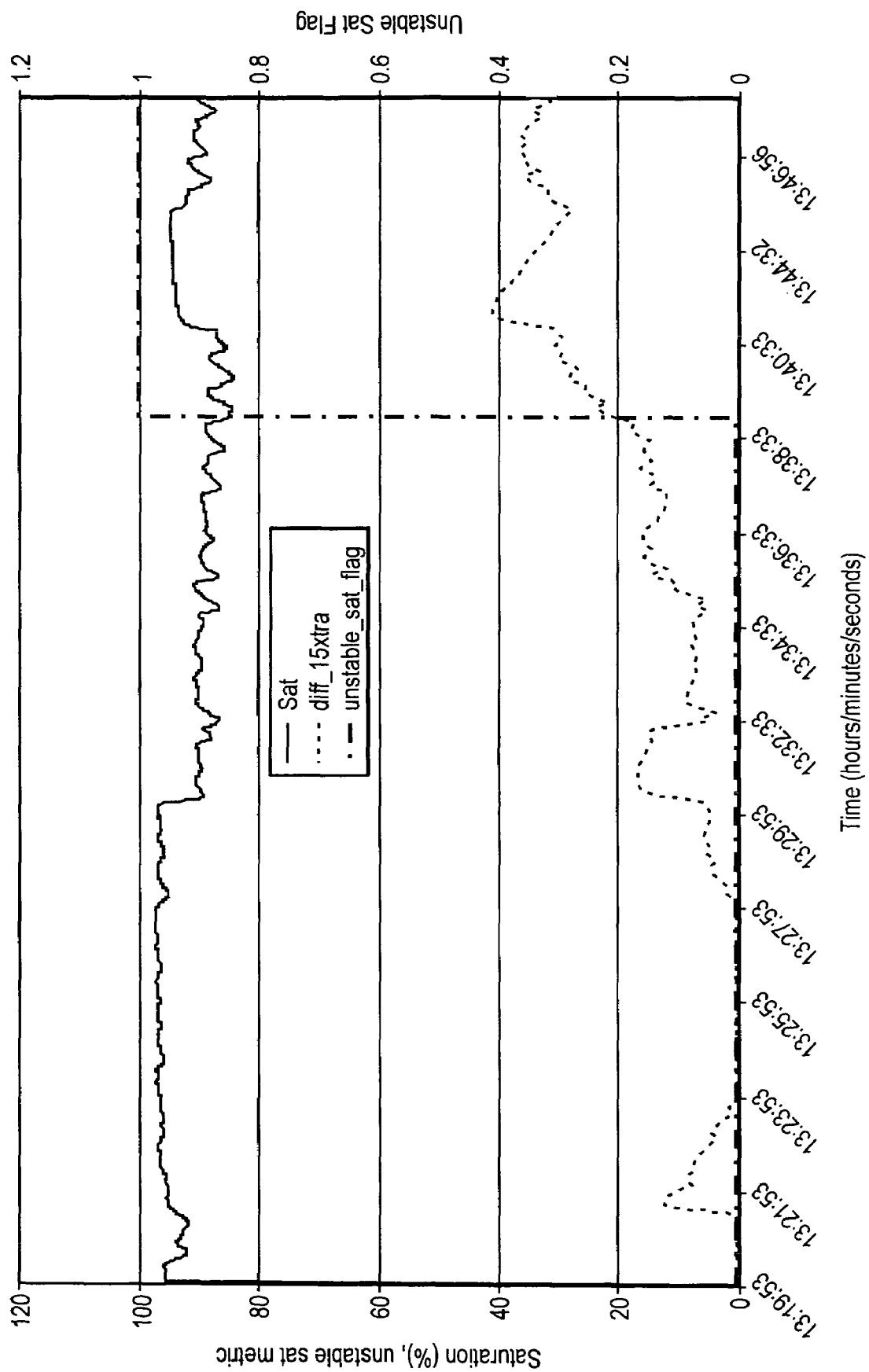
Figure 10:
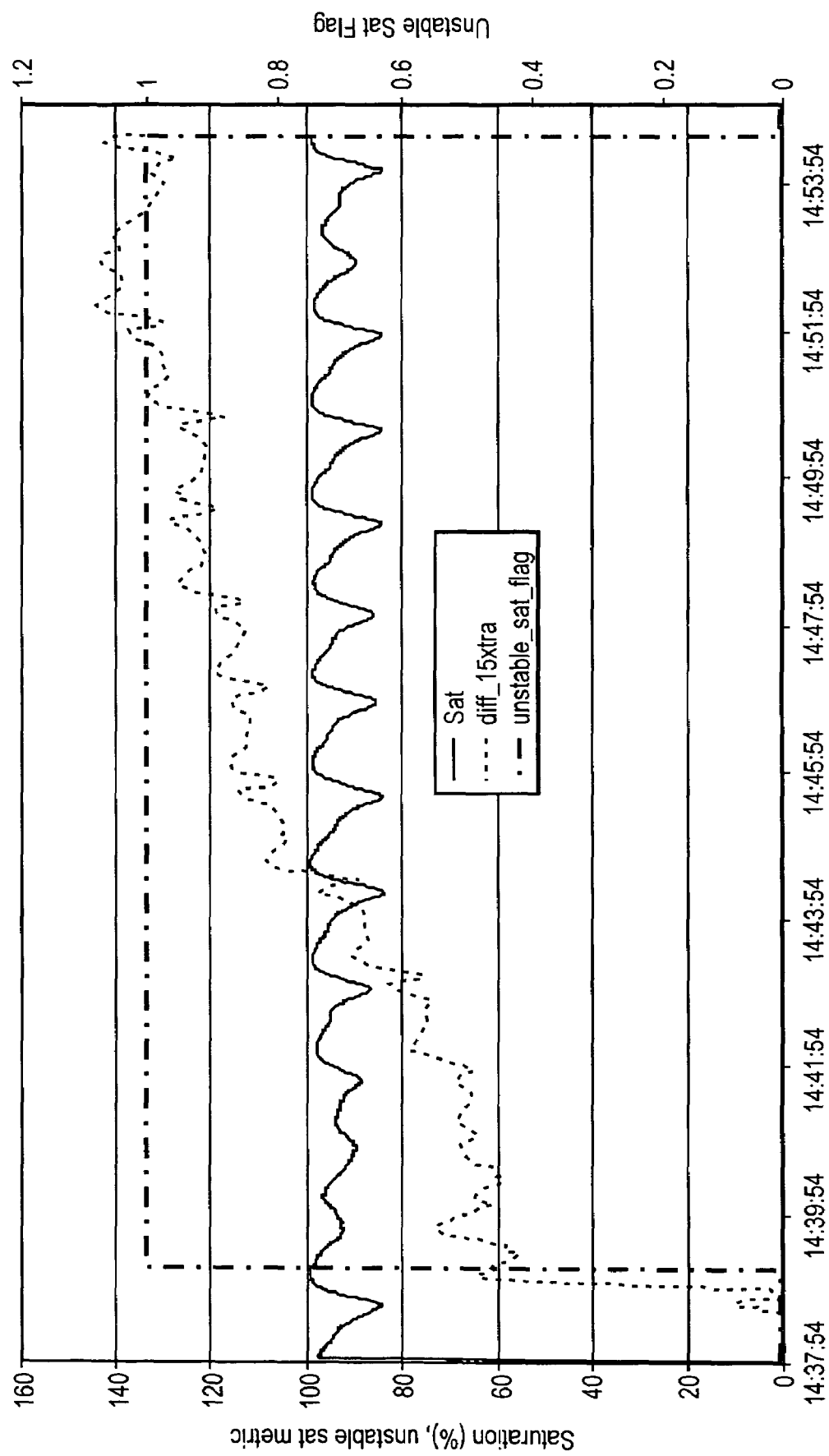

As set forth above, FIGS. 5-10 each correspond to a dataset representative of cyclic saturation variations. In particular, a saturation trace from a pulse oximeter and the value of a variable (unstable_sat_flag) indicative the presence of an unstable saturation condition are shown in each of FIGS. 5-10. FIG. 5 shows cyclic variations of approximately 4% that are identified after about two and a half minutes, at which time the value of the variable unstable_sat_flag transitions from a value of zero to a value of one. FIG. 6 shows cyclic variations of approximately 5% that are identified in about one and a half minutes. FIG. 7 shows cyclic variations of approximately 2% to 6% that are identified in about one and a half minutes. FIG. 8 shows cyclic variations of approximately 6% that are identified in about two minutes. In FIG. 9, variations occur in the middle third of the dataset. These variations are believed to be attributable to a change in the oximeter sensor or sensor site. Although cyclic saturation variations are not as regular as in the other cases, cyclic variations of approximately 4% to 5% are identified after about five minutes. The dataset represented in FIG. 10 shows cyclic variations of approximately 15% that are identified in about one minute.

In simulations with synthetic data, an exemplary embodiment of the present invention detected cyclic saturation variations of approximately 2% to 3% with a period in the range from one minute to five minutes. Cyclic variations of approximately 10% were detected in periods as short as 35 to 50 seconds. An exemplary embodiment of the present invention may be adapted to detect shorter saturation cycles that may occur in the case of infants. For example, metrics for one and ten second interval saturation changes may be evaluated. The averaging response time and thresholds may also be modified to achieve more (e.g., shorter interval) or less (e.g., longer interval) sensitive detection of unstable saturation behavior depending on the desired phenomena to be detected.

The following is a listing of exemplary programming code in accordance with one embodiment of the present invention:

```
#AWK script to evaluate unstable saturation behaviour characteristic of
#obstructive sleep apnea, based on saturation and quality metrics internal
# to the oximetry algorithm.
# initialize variables
BEGIN
{
  for (i = 0; i <= 15; i++)
  {
    sat_hist[i] = 0.0;
    sat_age_hist[i] = 0.0;
    mot_hist[i] = 0;
  }
  mean_diff_15 = 0.30;
  mean_diff_1 = 0.10;
  nz_sat_cnt = 0;
  diff_15_xtra = 0.0;
  diff_15_xtra_exceeds_10_cnt = 0;
  unstable_sat_flag = 0;
}
# The following section is invoked for each ASCII input line
# which is assumed to occur once per second
{
  #read saturation, saturation age, and motion flag (columns 3, 21, 25).
  sat_hist[0] = $3 * 1.0;
  sat_age_hist[0] = $21 * 1.0;
  mot_hist[0] = $25 * 1;
  #reinitialize variables when saturation is zero
  if (sat_hist[0] == 0.0)
  {
    for (i = 0; i <= 15; i++)
    {
      sat_hist[i] = 0.0;
      sat_age_hist[i] = 0.0;
      mot_hist[i] = 0;
    }
    mean_diff_15 = 0.30;
    mean_diff_1 = 0.10;
    nz_sat_cnt = 0;
    diff_15_xtra = 0.0;
    diff_15_xtra_exceeds_10_cnt = 0;
    unstable_sat_flag = 0;
  }
  else
  {
    nz_sat_cnt++;
  }
#update metrics when saturation has been non-zero for 15 seconds
  if ((sat_hist[0] > 0.0) && (sat_hist[15] > 0.0))
  {
    #update averaging response time (60 sec --> 5 minutes)
    fwt = 1.0 / nz_sat_cnt;
    if (nz_sat_cnt < 60)
      fwt = 1.0 / 60.0
    if (nz_sat_cnt > 300)
    fwt = 1.0 / 300.0;
    #compute and average 1-sec (short-term) saturation changes
    sat_diff_1 = 0.0;
    for (i = 0; i < 15; i++)
    {
      tmp = sat_hist[i] - sat_hist[i+1];
      if (tmp < 0.0)
      {
        tmp = 0.0 - tmp;
      }
      sat_diff_1 += tmp / 15.0;
    }
```

-continued

```
    mean_diff_1 += fwt * (sat_diff_1 - mean_diff_1)
    #compute 15-sec saturation change
    if (sat_age_hist[15] < sat_age_hist[0] + 5.0)
    {
      sat_diff_15 = sat_hist[0] - sat_hist[15];
    }
    #if saturation age has been getting younger due to
    #the cessation of artifact, then compute saturation change
    #over a slightly shorter interval
    else
    {
      sat_diff_15 = sat_hist[0] - sat_hist[14];
    }
    if (sat_diff_15 < 0.0)
    {
      sat_diff_15 = 0.0 - sat_diff_15;
    }
    #downweight saturation-change metric for very high
    #saturations.
    if (sat_hist[0] > 99.0)
    {
      sat_diff_15 -= 0.5 * (sat_hist[0] - 99.0);
    }
    #downweight saturation-change metric if motion artifact
    #was detected during the interval
    if ((mot_hist[0] > 0) || (mot_hist[7] > 0) ||
    (mot_hist[15] > 0))
        sat_diff_15 /= 2;
    #average 15-second saturation-change metric
    mean_diff_15 += fwt * (sat_diff_15 - mean_diff_15)
  }
  #combine the averaged 1-second and 15-second change metrics
  diff_15_xtra = 100.0 * (mean_diff_15 - 8.0 * mean_diff_1);
  if (diff_15_xtra < 0.0)
    diff_15_xtra = 0.0;
  if (diff_15_xtra > 10.0)
  {
    diff_15_xtra_exceeds_10_cnt++;
  }
  else
  {
    diff_15_xtra_exceeds_10_cnt = 0;
  }
  #update unstable saturation condition
  if ((unstable_sat_flag == 1) && (diff_15_xtra < 15.0))
  {
    unstable_sat_flag = 0;
  }
  if ((unstable_sat_flag == 0) && (diff_15_xtra > 20.0) &&
     (diff_15_xtra_exceeds_10_cnt > 15))
  {
    unstable_sat_flag = 1;
  }
  #move old data back in the buffers. Location [1] denotes 1 second
  #ago, location [15] denotes 15 seconds ago, etc.
  for (i = 15; i > 0; i--)
  {
    sat_hist[i] = sat_hist[i-1];
    sat_age_hist[i] = sat_age_hist[i-1];
    mot_hist[i] = mot_hist[i-1];
  }
  #print header line
  if (FNR == 1)
    printf("%s\t%s\t%s\t%s\tunstable_sat_flag\tdiff_15_xtra\n",
    $1, $3, $21, $25)
  #print output for each one-second ASCII input line, after line 1
  else
    printf("%s\t%s\t%s\t%s\t%u\t%0.2f\n",
      $1, $3, $21, $25, unstable_sat_flag, diff_15_xtra);
}
# End of AWK script
```

The exemplary programming code may be implemented in a pulse oximetry software algorithm that allows analysis of large quantities of data in order to detect unstable oxygen saturation of a patient. Those of ordinary skill in the art will appreciate that many other programming scripts can be used and yet still perform an analysis of statistical variations in blood oxygenation so as to detect unstable oxygen saturation in accordance with embodiments of the present invention. The exemplary program code above includes artifact dectection and saturation age quality metrics to reduce undesirable effects of non-physiologic artifacts of the type illustrated in FIG. 3.

An exemplary embodiment of the programming script listed above has been used to post-process oximetry data from each of the 113 cases in the sample database referred to above to evaluate unstable oxygen saturation behavior characteristic of obstructive sleep apnea. The goal of this analysis was to determine whether the manual analysis that distinguished cyclic saturation variations from other artifactual variations could be confirmed using software with an acceptable degree of reliability and response time (e.g., response time sufficiently fast to permit real-time analysis of patient data).

The outputs of the programming script listed above include the time series $SpO_2$ input denoted by the unbroken saturation "Sat" trace (FIGS. 5-10), the diff__15_extra variable referred to in the exemplary program code, which quantifies the degree to which the data is above the diagonal threshold line 34 (FIG. 4). The unstable_sat_flag referred to in the example program code is set to one when the specified thresholds for the diff__15_extra variable are exceeded. Moreover, the detection of a cyclic pattern of unstable oxygen saturation may be conditioned upon exceeding a single threshold or multiple thresholds. Additionally, statistical metrics may be modified depending on a magnitude of oxygen saturation being evaluated. In the exemplary program code set forth above, the diff__15_extra variable computes and averages the absolute values of the one and fifteen second interval saturation changes, where the averaging has a response time that starts at one minute and gradually lengthens to five minutes, and determines if the threshold is exceeded.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, "exceeding a threshold" can mean being either above or below the threshold, depending on the circumstances and the parameter being measured. Therefore, the above description should not be taken as limiting the scope of the invention which is defined by the appended claims.

What is claimed is:

1. A method for automatic detection of unstable oxygen saturation of a patient using a pulse oximeter, the method performed with a processor and comprising:
   receiving at least a single time series input of oxygen saturation values;
   computing at least two statistical metrics based on statistical properties of the single time series input of oxygen saturation values, wherein the at least two statistical metrics in combination are sensitive to both magnitude and frequency range of oxygen saturation variations; and
   determining if an unstable oxygen saturation condition exists based on the at least two statistical metrics.

2. The method as in claim 1, further comprising averaging the statistical metrics.

3. The method as in claim 2, wherein determining if an unstable oxygen saturation condition exists comprises computing a value based on a relationship between the statistical metrics.

4. The method as in claim 3, further comprising providing an output if the computed value exceeds a threshold value.

5. The method as in claim 4, comprising providing an indication that cyclic saturation variations have been identified as the output.

6. The method as in claim 4, wherein the output comprises sounding an audio alarm.

7. The method as in claim 4, wherein the output comprises displaying a visual alert.

8. The method as in claim 4, wherein the threshold value varies over a range from about 60% to about 90% of a ratio of time intervals used for quantifying saturation changes.

9. The method as in claim 1, wherein the statistical metrics are selected to be sensitive to ventilation or airway instability.

10. The method as in claim 1, wherein the statistical metrics are selected to be sensitive to sleep apnea.

11. The method as in claim 1, wherein at least one statistical metric comprises a magnitude of saturation changes over 0.5 to 5 second intervals.

12. The method as in claim 11, wherein a second statistical metric comprises a magnitude of saturation changes over 10 to 30 second intervals.

13. The method as in claim 1, wherein at least one statistical metric comprises a skewness of the single time series input of oxygen saturation values.

14. The method as in claim 1, wherein at least one statistical metric comprises a kurtosis of the single time series input of oxygen saturation values.

15. The method as in claim 1, wherein the statistical metrics are selected to be sensitive to cyclic saturation variations with a period of at least 35 seconds to 5 minutes.

16. The method as in claim 1, further comprising modifying the statistical metrics based on one or more signal quality metrics.

17. The method as in claim 1, further comprising modifying the statistical metrics depending on a magnitude of the oxygen saturation values.

18. The method as in claim 1, further comprising determining whether the oxygen saturation values correspond to unstable oxygen saturation by comparing the oxygen saturation values to multiple thresholds.

19. A method for automatic detection of unstable oxygen saturation of a patient using a pulse oximeter, the method performed with a processor and comprising:
   receiving at least a single time series input of oxygen saturation values;
   computing at least two statistical metrics based on statistical properties of the single time series input of the oxygen saturation values;
   modifying the statistical metrics based on one or more signal quality metrics;
   averaging the statistical metrics;
   computing a value indicative of unstable oxygen saturation based on a relationship between the statistical metrics; and
   providing an output if the computed value exceeds a threshold value.

20. A patient monitoring system for automatically detecting unstable oxygen saturation of a patient using a pulse oximeter, the system comprising:
   a pulse oximeter for measuring at least a single time series input of oxygen saturation values; and
   a processor programmed to compute at least two statistical metrics based on statistical properties of the single time series input of oxygen saturation values, wherein the at least two statistical metrics in combination are sensitive to both magnitude and frequency range of oxygen saturation variations and programmed to determine if an unstable oxygen saturation condition exists based on the at least two metrics.

21. The system as in claim 20, wherein the processor is further programmed to average the statistical metrics.

22. The system as in claim 20, wherein the processor is further programmed to compute a value based upon a relationship between the statistical metrics.

23. The system as in claim 22, wherein the processor is further programmed to provide an output if the computed value exceeds a threshold value.

24. The system as in claim 23, wherein the statistical metrics are associated with one of cyclic saturation variations, ventilation or airway instability, and sleep apnea.

25. The system as in claim 20, wherein at least one statistical metric comprises a skewness of the single time series input of oxygen saturation values.

26. The system as in claim 20, wherein at least one statistical metric comprises a kurtosis of the single time series input of oxygen saturation values.

27. The system as in claim 20, wherein the statistical metrics are modified depending on a magnitude of the oxygen saturation values.

28. The system as in claim 20, wherein the oxygen saturation values are determined to correspond to unstable oxygen saturation by comparing the oxygen saturation values to multiple thresholds.

29. A tangible computer-readable storage medium having a computer-readable program embodied therein for directing operation of a computer system, the computer system including a communications system, a processor, and a memory device, wherein the computer-readable program includes instructions for operating the computer to automatically detect unstable oxygen saturation in a patient in accordance with the following:

receiving at least a single time series input of oxygen saturation values;

computing at least two statistical metrics based on statistical properties of the single time series input of oxygen saturation values, wherein the at least two statistical metrics in combination are sensitive to both magnitude and frequency range of oxygen saturation variations; and determining if an unstable oxygen saturation condition exists based on the at least two statistical metrics.

\* \* \* \* \*